United States Patent
Shikhman et al.

[11] Patent Number: 5,911,729
[45] Date of Patent: Jun. 15, 1999

[54] ELECTROCAUTERY CORING USING SOLID NEEDLE

[75] Inventors: Oleg Shikhman, Fairfield; James Correia, Shelton, both of Conn.; Thomas J. Pacala, Corona del Mar, Calif.

[73] Assignee: United States Surgical Corporation, Norwalk, Conn.

[21] Appl. No.: 08/910,713

[22] Filed: Aug. 13, 1997

[51] Int. Cl.⁶ .................................................. A61B 17/14
[52] U.S. Cl. .......................... 606/181; 606/108; 606/182; 606/27; 606/28
[58] Field of Search .................................. 606/181, 167, 606/182, 15, 166, 108, 27, 28; 128/303.1; 604/22, 14, 15

[56] References Cited

U.S. PATENT DOCUMENTS

| | | |
|---|---|---|
| 4,658,817 | 4/1987 | Hardy .................................. 128/303.1 |
| 4,688,569 | 8/1987 | Rabinowitz . |
| 4,878,493 | 11/1989 | Pasternak et al. . |
| 4,998,934 | 3/1991 | Berstein . |
| 5,330,470 | 7/1994 | Hagen . |
| 5,421,819 | 6/1995 | Edwards et al. . |
| 5,435,805 | 7/1995 | Edwards et al. . |
| 5,458,597 | 10/1995 | Edwards et al. . |
| 5,470,308 | 11/1995 | Edwards et al. . |
| 5,470,309 | 11/1995 | Edwards et al. . |
| 5,486,161 | 1/1996 | Lax et al. . |
| 5,507,743 | 4/1996 | Edwards et al. . |
| 5,514,130 | 5/1996 | Baker . |
| 5,527,279 | 6/1996 | Imran . |
| 5,531,743 | 7/1996 | Nettekoven et al. . |
| 5,536,267 | 7/1996 | Edwards et al. . |
| 5,554,110 | 9/1996 | Edwards et al. . |
| 5,556,377 | 9/1996 | Rosen et al. . |
| 5,558,672 | 9/1996 | Edwards et al. . |
| 5,569,241 | 10/1996 | Edwards . |
| 5,575,788 | 11/1996 | Baker et al. . |
| 5,582,589 | 12/1996 | Edwards et al. . |
| 5,591,125 | 1/1997 | Edwards et al. . |
| 5,591,159 | 1/1997 | Taheri . |
| 5,599,295 | 2/1997 | Rosen et al. ............................. 604/22 |
| 5,607,389 | 3/1997 | Edwards et al. . |
| 5,700,259 | 12/1997 | Negus et al. . |
| 5,713,894 | 2/1998 | Murphy-Chutorian et al. .......... 606/15 |
| 5,810,836 | 9/1998 | Hussein et al. ........................ 606/108 |

*Primary Examiner*—Michael Buiz
*Assistant Examiner*—Lie N. Ngo

[57] ABSTRACT

The present disclosure relates to a method apparatus for transmyocardial revascularization. The apparatus includes an incision needle for creating an incision within a patient's heart to define a channel, and an electrocautery assembly operatively associated with the incision needle for transferring thermal energy to an inner surface of the channel to reduce bleeding therefrom and to prevent the channel from closing. Preferably, thermal energy is not transferred to the epicardium to create a flap or channel cap after the cylindrical incision needle is removed from relevant tissue to reduce bleeding from the channel.

9 Claims, 4 Drawing Sheets

ELECTROCAUTERY CORING USING SOLID NEEDLE

BACKGROUND

1. Technical Field

The present disclosure relates to a method for transmyocardial revascularization (TMR) and apparatus for implementing the same.

2. Background of the Related Art

TMR is a known procedure for producing channels of small diameters within the myocardium, which channels extend into the ventricle. Such channels are believed to facilitate delivery of blood directly from the ventricle to oxygen starved areas of the heart. TMR is typically used on patients with ischemic heart disease who are not candidates for coronary artery bypass or percutaneous transluminal angioplasty.

During a TMR procedure, typically dozens of channels are created from the epicardium, through the myocardium and endocardium and into the ventricle, with each channel being of sufficiently small diameter such that the end portions of the channels at the epicardium can be closed by blood clotting. The channels are preferably created by employing either a mechanical coring apparatus or an advancing lasing device. With either technique, an important objective is to produce channels that remain patent in the long term and which do not close up due to fibrosis and/or scarring.

With traditional TMR procedures, a technique for stopping the bleeding from each channel at the epicardium after channel formation entails applying pressure to the opening of the just-formed channel. Pressure is typically applied by the finger of the surgeon or assistant during open heart surgery, or with an endoscopic instrument when the procedure is performed endoscopically. In either case, since pressure is applied to each channel opening for at least several seconds, and it is impractical to begin forming another channel until the bleeding is stopped from the previous channel, the overall TMR procedure wherein typically dozens of channels are formed is undesirably prolonged by the time expended on applying pressure to each channel.

Accordingly, a need exists for a TMR procedure wherein the time spent to stop the blood flow from each of the individual transmyocardial channels is reduced or eliminated and the channels are prevented from closing, thereby increasing the likelihood of success of each operation and saving lives.

A need also exists to provide cost effective instruments for performing TMR.

SUMMARY

The present disclosure is directed to a method for performing TMR. The method includes the steps of creating an incision in the patient's heart by advancing an incision creating device from the epicardium through the myocardium and into a ventricle of the heart, and transferring thermal energy from the incision creating device to the heart tissue by means of an electrocautery structure. As a result, heart tissue immediately surrounding the newly created channel is irradiated with thermal energy to reduce bleeding from the incision and to prevent or inhibit the channel from closing subsequent to removal of the incision creating device.

The present disclosure also relates to an apparatus for implementing the above TMR method. The apparatus includes an incision needle for creating an incision within a patient's heart to define a channel, and an electrocautery assembly operatively associated with the incision needle for transferring thermal energy to an inner surface of the channel to reduce bleeding therefrom and to prevent or inhibit the channel from closing.

Advantageously, with the presently disclosed methods and apparatus, blood clotting can occur rapidly and, combined with closure of the channel at the epicardial surface, can reduce the time expended for the step of applying pressure to the channel opening following formation of each channel. Also, the presently disclosed device is relatively inexpensive, as compared to, for example, lasing devices.

BRIEF DESCRIPTION OF THE DRAWINGS

Various preferred embodiments are described herein with reference to the drawings, wherein.

DETAILED DESCRIPTION OF PREFERRED EMBODIMENTS

Figure 1:
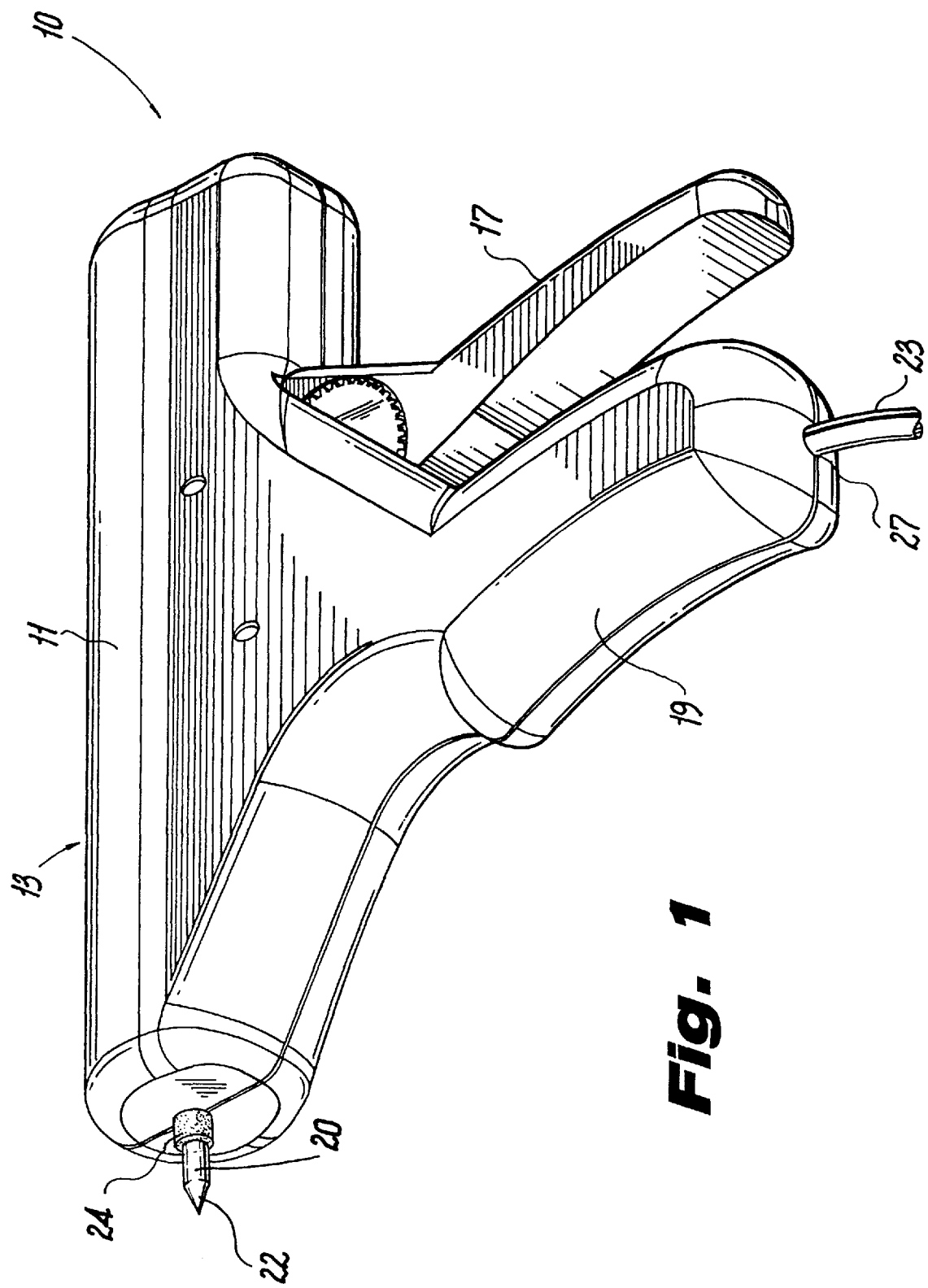
FIG. 1 shows an embodiment of a mechanical incision device having a solid incision needle in accordance with the present disclosure.

Preferred embodiments of TMR methods and apparatus will now be described in detail with reference to the drawings, in which like reference numerals designate identical or corresponding elements.

Referring now to FIG. 1, an illustrative mechanical incision device 10 is shown which can be employed to produce a channel during heart surgery. Device 10 is a modified design of a mechanical coring device described in detail in commonly assigned, copending U.S. patent application Ser. No. 08/650,485, filed on May 13, 1996 entitled CORING DEVICE AND METHOD, to Pacala et al. Pacala et al. describes a mechanical coring device for coring body tissue to define reproducible patient channels by utilizing a coring member that is rotatable and linearly advanceable at coordinated predetermined rates. A cauterization feature is also disclosed therein.

As shown in FIG. 1 of the present disclosure, device 10 has a solid incision needle 20, described in further detail below, having a distal cutting portion 22 for creating a channel in heart tissue. Housing 13 includes an elongated body portion 11 defining the longitudinal axis of device 10 and a stationary handle 19 projecting from elongated body portion 11. A movable trigger 17 is pivotally connected to housing 13 adjacent stationary handle 19 forming a pistol type grip. In a storage position, with trigger 17 at rest, needle 20 is preferably retracted back into housing 13 so that the sharp cutting edge does not protrude, thereby preventing accidental injury. An opening 27 allows passage of power supply cable 23 into the housing to power the linear advancement and rotation of the incision needle 20 when trigger 17 is depressed. Another opening (not shown) allows for connection of device 10 to a power source for energizing an electrocautery assembly within housing 13.

Figure 2:
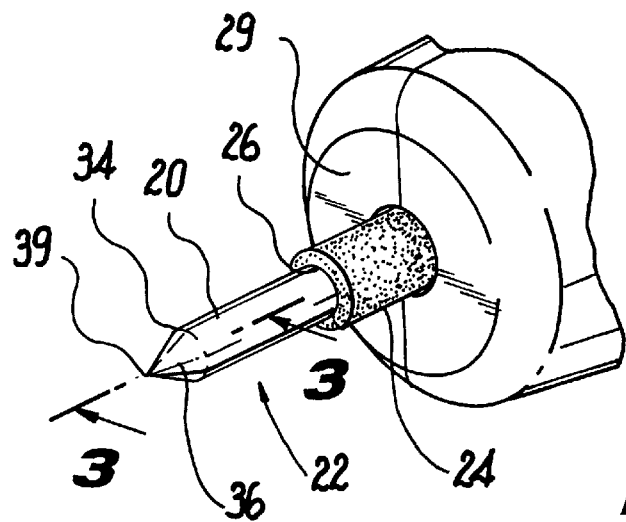
FIG. 2 is an enlarged perspective view of the distal end of the mechanical incision device of FIG. 1.

Referring to FIG. 2, an enlarged perspective view of the distal end 29 of the mechanical incision device is illustrated. A sleeve 24 extends from the distal end of elongated body portion 11 defining an opening 26 for needle 20 to pass therethrough. Sleeve 24 is preferably constructed from non-conductive material to prevent thermal energy from being transferred to the incision opening during the electrocautery operation as described below. The solid needle 20 passes through sleeve 24 as the trigger 17 is depressed and creates an incision as the device 10 is moved longitudinally during operation.

Figure 3:
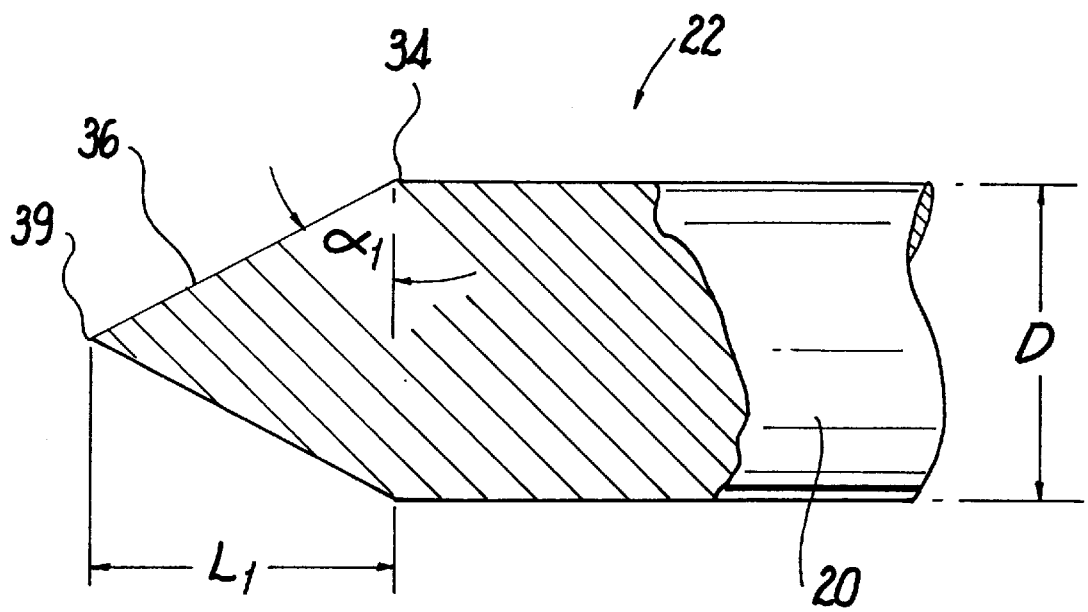
FIG. 3 is a cross-sectional view of the distal end of the solid incision needle of FIG. 1 taken along line 3—3 in FIG. 2.
Figure 4:
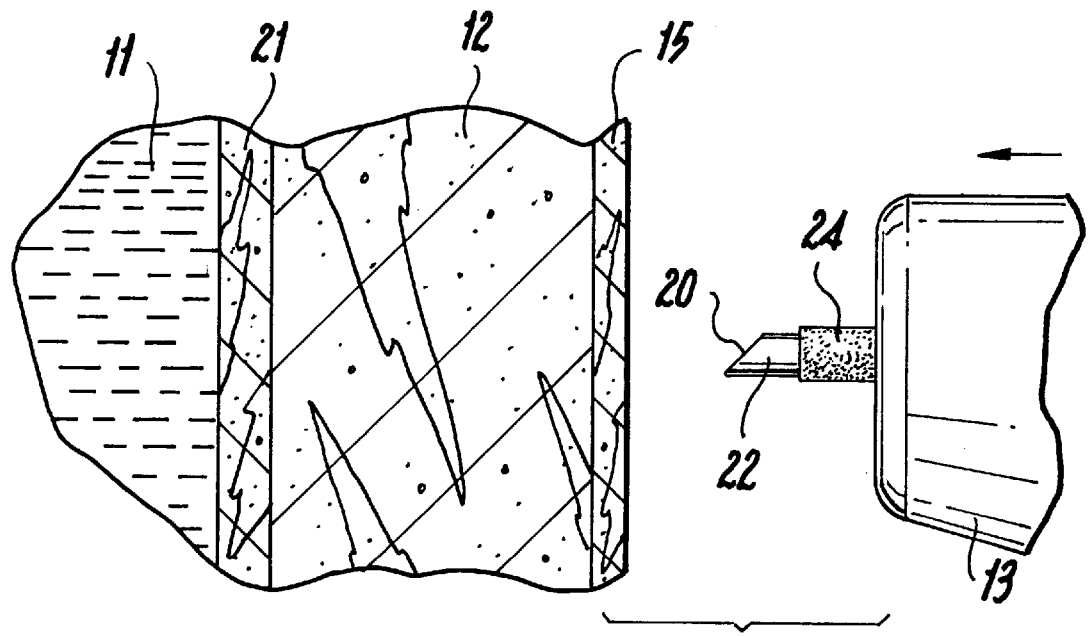
FIGS. 4–7 are cross-sectional views of the mechanical incision device of FIG. 1 creating a channel in accordance with the present disclosure.
Figure 5:
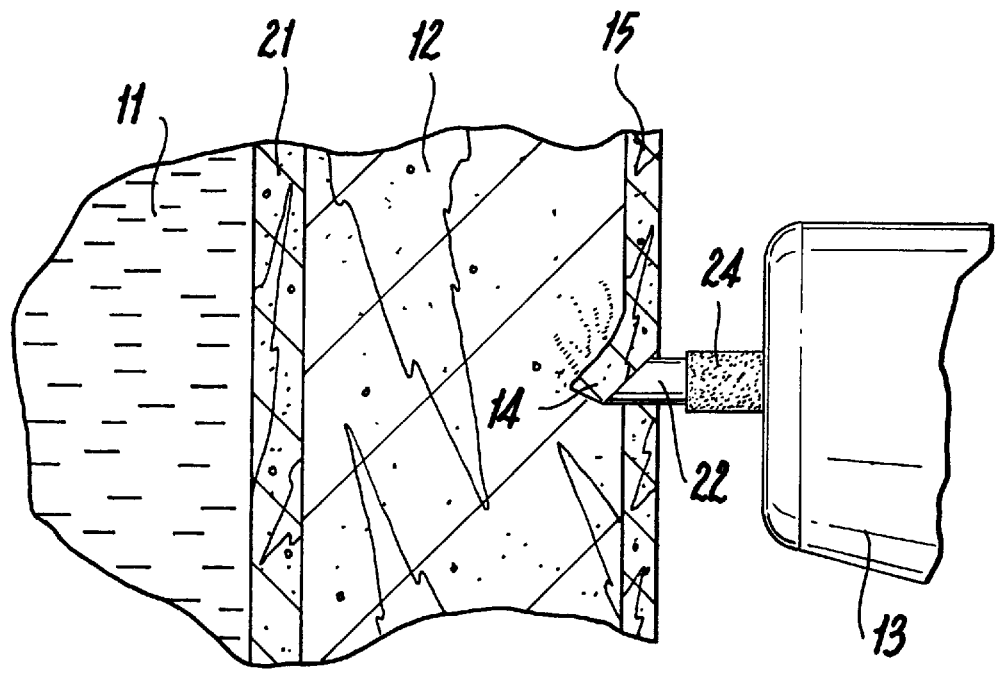

A preferred configuration for the cutting portion 22 of solid incision needle 20 is shown more clearly in the cross-sectional view of FIG. 3. Referring to FIG. 3, incision needle 20 has a cutting portion 22 which is of a beveled shape defining a peak 39 and trough 34. A first beveled portion 36 extends from trough 34 to peak 39. Peak 39 is an axial distance $L_1$ away from trough 34. Beveled portion 36 is defined by an angle $\alpha_1$ which may be in the range of 25–35°. The thickness or diameter D of the needle 20 is in the range of about 2 mm. Diameter D should be sufficiently large to enable heart tissue to be pushed aside as the cutting end 22 penetrates. Preferably, the incision needle 20 is solid to prevent the coring of heart tissue. Alternately, needle 20 can have a single bevel, as shown in FIGS. 4–8.

Referring now to the cross sectional views of FIGS. 4–8, a TMR procedure in accordance with the present disclosure is initiated by inserting cutting portion 22 a predetermined distance L into the heart tissue 12, whether by automatic or manual insertion of cutting portion 22. As cutting portion 22 penetrates, heart tissue is pushed aside by the walls of the cutting portion 22, and compresses against the adjoining tissue. Incision needle 20 can be simultaneously advanced and rotated in order to form a channel 18 having a substantially uniform diameter.

Figure 6:
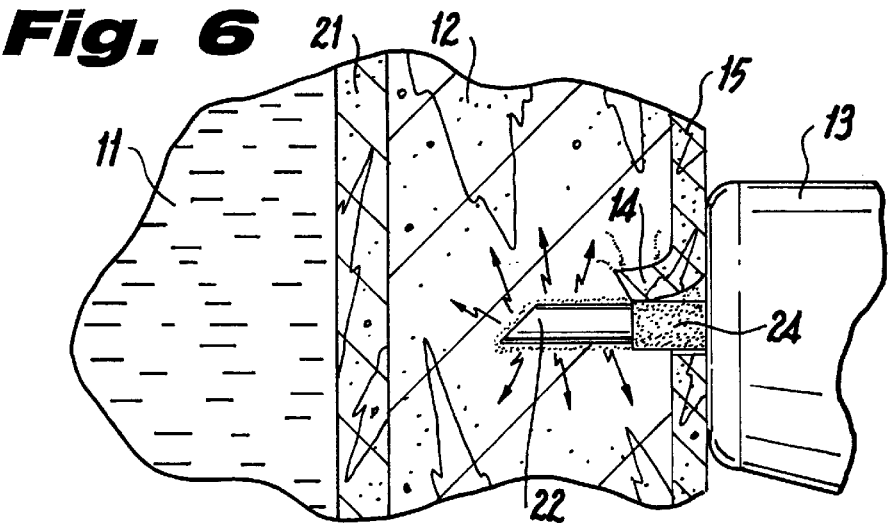
Figure 7:
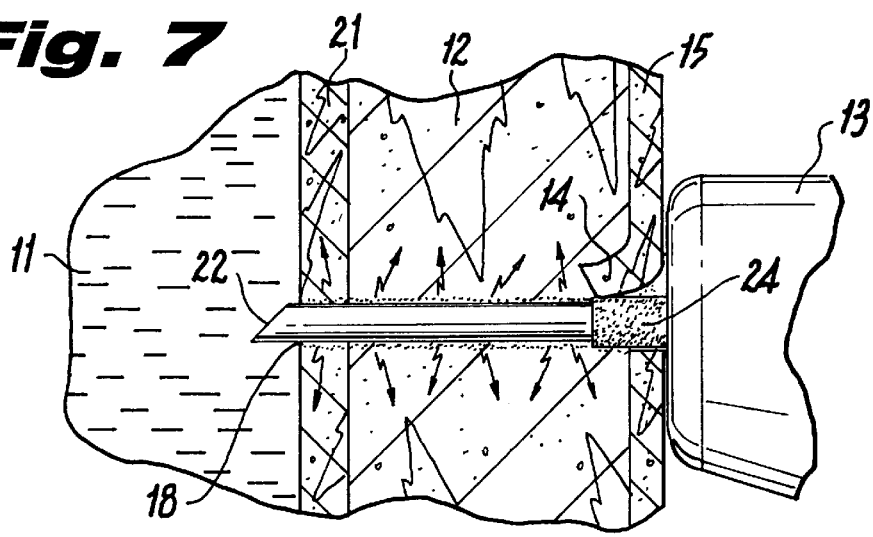

Once the cutting portion 22 has passed the epicardium/myocardium border, the electrocautery operation is initiated (FIG. 6). During the electrocautery operation, thermal energy is transferred to the heart tissue except where protected by sleeve 24, such as at flap 14. The power source can provide continuous power to the electrocautery assembly within device 10 or provide a series of power pulses as is known in the art. Both bipolar and monopolar systems can be used. Furthermore, ultrasonic or other vibrational energy can be transmitted by the needle to impart a desired affect to the surrounding tissue.

Figure 8:
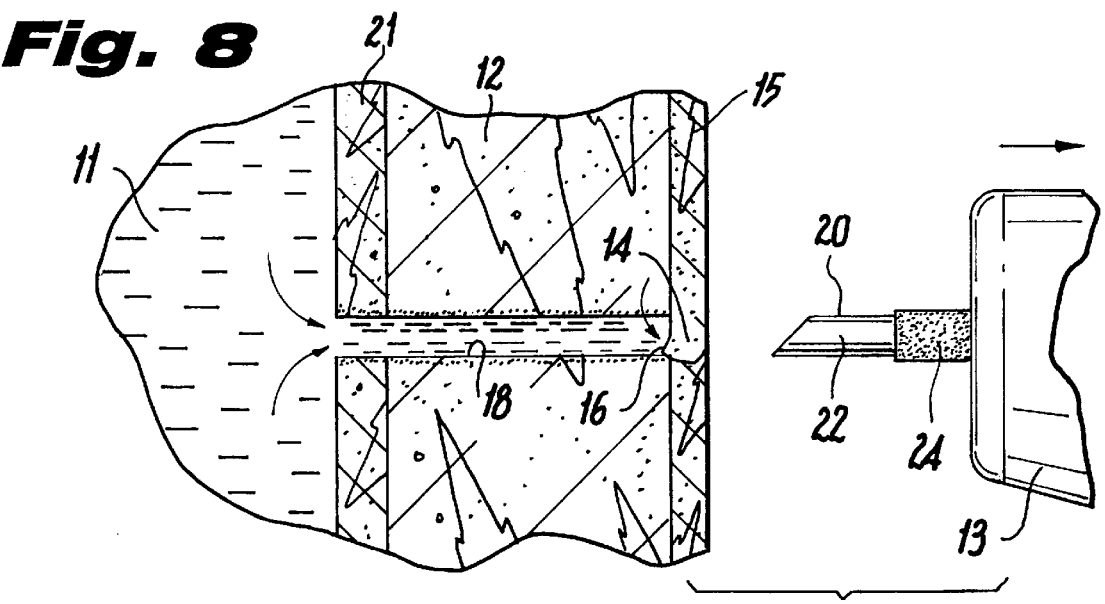
FIG. 8 is a cross-sectional view of the channel created by the mechanical incision device of FIG. 1.

After incision needle 20 is removed, the myocardial/endocardial tissue flap 14 that was pushed aside recoils to its original position, resulting in the channel 18 with flap 14 as a cap in FIG. 8. The operator can then immediately begin producing another channel without applying pressure to the previously formed channel 18. In addition, bleeding is prevented or substantially reduced by the flap or channel cap 14 formed at the epicardium-myocardium border by the tissue that was pushed aside during the initial insertion of solid incision needle 20 into the heart tissue.

Referring to FIG. 8, a cross-sectional view of the transmyocardial channel 18 which is formed by methods and apparatus in accordance with the present disclosure is shown. Channel 18 is generally cylindrical and extends from epicardium 15 through myocardium 12 and endocardium 21 into ventricle 11. The channel 18 is "capped" by the flap 14 which mainly includes epicardial tissue 15. Flap 14 is sealed to the myocardium 12 and epicardium 15 at adjoining interface 16 by blood clotting.

It will be understood that various modification can be made to the embodiments disclosed herein. For instance, wand-type mechanical incision devices can alternatively be utilized rather than the "gun" type disclosed above. Additionally, the procedure may be performed endoscopically with appropriate design of the mechanical incision device. Therefore, the above description should not be construed as limiting, but merely as exemplifications of preferred embodiments. Those skilled in the art will envision other modifications within the scope and spirit of the claims appended hereto.

What is claimed is:

1. A method of performing transmyocardial revascularization (TMR) comprising the steps of:
   providing a solid needle;
   creating a channel in a patient's myocardium by advancing the solid needle from the epicardium, through the myocardium and into the ventricle;
   transferring thermal energy via the solid needle to an inner surface of the channel; and
   protecting a portion of the heart tissue from thermal energy by providing a non-conductive member that surrounds at least a portion of said solid needle that would otherwise be in contact with heart tissue.

2. The method according to claim 1, wherein said step of transferring thermal energy is performed by an electrocautery assembly associated with the solid needle.

3. An apparatus for performing transmyocardial revascularization (TMR) comprising:
   a mechanical incising device having an advanceable solid needle for creating a channel within a patient's myocardium; and
   a hollow cylindrical, non-conductive member surrounding a portion of said solid needle as said solid needle advances within said myocardium to form the channel, said hollow cylindrical, non-conductive member being adapted to contact a portion of the heart tissue located proximally from the solid needle as the solid needle advances within the myocardium to prevent said portion of the heart tissue from being cauterized as thermal energy is transferred to the solid needle.

4. The apparatus according to claim 3, wherein a distal end of said solid needle is beveled.

5. The apparatus according to claim 3, wherein a diameter of said solid needle is approximately 2 mm.

6. The apparatus according to claim 3, further comprising an electrocautery assembly operatively associated with said solid needle.

7. The apparatus according to claim 3, wherein said hollow cylindrical member is non-conductive.

8. An apparatus for performing transmyocardial revascularization (TMR) comprising:
   a mechanical incising device having an advanceable solid needle for creating a channel within a patient's heart tissue, said solid needle being operatively associated with an advancing mechanism of said mechanical incising device for advancing the solid needle from the epicardium, through the myocardium and into the ventricle; and
   a hollow non-conductive cylindrical member surrounding a proximal portion of said solid needle as said solid needle advances within said myocardium to form the channel.

9. The apparatus according to claim 8, further comprising an electrocautery assembly operatively associated with said solid needle.

* * * * *